(12) United States Patent
Dos Santos et al.

(10) Patent No.: US 10,485,630 B2
(45) Date of Patent: Nov. 26, 2019

(54) SYSTEMS AND METHODS FOR A HAND-CONTROLLABLE SURGICAL ILLUMINATION DEVICE

(71) Applicant: Novartis AG, Basel (CH)

(72) Inventors: Cesario Pereira Dos Santos, Costa Mesa, CA (US); Alireza Mirsepassi, Irvine, CA (US); Michael J. Papac, North Tustin, CA (US); Ryan Makoto Takakawa, Aliso Viejo, CA (US)

(73) Assignee: Novartis AG, Basel (CH)

( * ) Notice: Subject to any disclaimer, the term of this patent is extended or adjusted under 35 U.S.C. 154(b) by 234 days.

(21) Appl. No.: 15/377,238

(22) Filed: Dec. 13, 2016

(65) Prior Publication Data

US 2017/0172694 A1 Jun. 22, 2017

Related U.S. Application Data

(60) Provisional application No. 62/267,975, filed on Dec. 16, 2015.

(51) Int. Cl.
| | |
|---|---|
| *A61B 1/06* | (2006.01) |
| *A61B 90/30* | (2016.01) |
| *A61B 3/00* | (2006.01) |
| *A61F 9/007* | (2006.01) |
| *F21V 23/04* | (2006.01) |
| *F21V 8/00* | (2006.01) |

(52) U.S. Cl.
CPC ............ *A61B 90/30* (2016.02); *A61B 3/0008* (2013.01); *A61F 9/007* (2013.01); *F21V 23/0435* (2013.01); *G02B 6/0008* (2013.01); *A61B 2090/306* (2016.02)

(58) Field of Classification Search
CPC . A61B 2090/306; A61B 90/30; A61B 3/0008; A61F 9/007; G02B 6/0008
See application file for complete search history.

(56) References Cited

U.S. PATENT DOCUMENTS 6,540,390 B2  4/2003  Toth et al.
8,118,790 B2  2/2012  Dacquay et al.
(Continued)

FOREIGN PATENT DOCUMENTS

EP  0424686 A1  5/1991
EP  1522290 A1  4/2005
(Continued)

*Primary Examiner* — Andrew J Coughlin

(57) ABSTRACT

An exemplary illumination system is provided herein for use in performing an ophthalmic surgical procedure. The illumination system may include a body configured to be held by a hand of a user. The body may include an outer surface and an inner surface that defines an inner chamber. The exemplary illumination system may further include an elongate tubular member extending from a distal end of the body, which may have an illumination path within a lumen of the elongate tubular member, and an illumination source coupled to the illumination path through an optical fiber extending between the body and a surgical console. The exemplary illumination system may include a plurality of illumination controls disposed on the outer surface of the body. A first illumination control may permit the user to selectively control an adjustable illumination level between a high intensity state and a low intensity state.

21 Claims, 9 Drawing Sheets

(56) References Cited

U.S. PATENT DOCUMENTS

| | | |
|---|---|---|
| 8,172,834 B2 | 5/2012 | Bhadra et al. |
| 8,371,695 B2 | 2/2013 | Papac et al. |
| 9,962,226 B2 | 5/2018 | Brennan et al. |
| 10,016,248 B2 | 7/2018 | Mirsepassi et al. |
| 2002/0126501 A1* | 9/2002 | Toth ................. A61B 5/0084 362/552 |
| 2004/0004846 A1 | 1/2004 | Steen et al. |
| 2007/0049926 A1* | 3/2007 | Sartor ............. A61B 18/1402 606/42 |
| 2008/0004608 A1 | 1/2008 | Dacquay et al. |
| 2009/0146583 A1* | 6/2009 | Bhadri ............. A61B 3/0008 315/294 |
| 2009/0163897 A1 | 6/2009 | Skinner |
| 2010/0198200 A1 | 8/2010 | Horvath |
| 2011/0105999 A1 | 5/2011 | Akahoshi |
| 2012/0041461 A1 | 2/2012 | McCollam |
| 2015/0144514 A1* | 5/2015 | Brennan ........... A61F 9/00736 206/363 |
| 2016/0346058 A1 | 12/2016 | Bacher et al. |
| 2017/0172694 A1 | 6/2017 | Dos Santos et al. |
| 2018/0140179 A1 | 5/2018 | LaBelle et al. |
| 2018/0140373 A1 | 5/2018 | Dos Santos et al. |

FOREIGN PATENT DOCUMENTS

| | | | |
|---|---|---|---|
| WO | 9613216 | A1 | 5/1996 |
| WO | 0059396 | A1 | 10/2000 |

\* cited by examiner

SYSTEMS AND METHODS FOR A HAND-CONTROLLABLE SURGICAL ILLUMINATION DEVICE

TECHNICAL FIELD

The present disclosure is directed to surgical devices, systems, and methods. More particularly, but not by way of limitation, the present disclosure is directed to devices, systems, and methods of providing controls on an illumination device for illuminating an interior of the eye during an ophthalmic surgical procedure.

BACKGROUND

Microsurgical procedures frequently require precision cutting and/or removal of various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. The cutting and removal of membranes may be particularly difficult in some delicate operations, such as mobile tissue management (e.g., cutting and removal of vitreous near a detached portion of the retina or a retinal tear) and vitreous base dissection.

Microsurgical procedures, such as those in the posterior segment of the eye, typically require numerous incisions to access the interior of the eye. Each additional incision may create risk for complications during the procedure and/or recovery. Various tools are inserted through the incisions for use by a user, such as a surgeon or other medical professional, while performing the procedure. Among the various tools is an illuminator, which may be inserted through one of the incisions. The illuminator lights the surgical field. Deploying the illuminator in the surgical field requires time and effort on the user's part to properly place the illuminator and affix the associated cables to keep them stationary. Additionally, as a surgeon moves through the various steps of a surgical procedure, the illumination requirements may change. For example, the illumination may need to be attenuated for a brief period to allow to surgeon to view other aspects of the tissues within the eye.

Current approaches to providing for changes in illumination require the surgeon to look up from the surgical view to interact with a surgical console or require the surgeon to communicate with an assistant, who then interacts with the surgical console to affect the desired changes. Such actions may cause a disruption in the flow of a surgical procedure, which may decrease the efficiency and efficacy of the procedure.

SUMMARY

The present disclosure is directed to exemplary illuminated microsurgical instruments and to methods of use of such instruments. The instruments may include a microsurgical instrument and an optical fiber for delivering light to a surgical site.

Exemplary surgical systems are provided herein. An exemplary illumination system for use in performing an ophthalmic surgical procedure may include a body that may be configured to be held by a hand of a user, the body may include an outer surface and an inner surface, the inner surface defining an inner chamber. The exemplary illumination system may further include an elongate tubular member extending from a distal end of the body, which may have an illumination path within a lumen of the elongate tubular member, and an illumination source coupled to the illumination path through an optical fiber extending between the body and a surgical console. The exemplary illumination system may include a plurality of illumination controls disposed on the outer surface of the body. A first illumination control may permit the user to selectively control an adjustable illumination level between a high intensity state and a low intensity state.

An exemplary illumination device is provided herein. One exemplary illumination device may be configured to provide illumination in a body cavity during a surgical procedure. The exemplary illumination device may include a body configured to be held by a hand of a user. The body may include an outer surface and an inner surface, which may define an inner chamber. The exemplary illumination device may include an elongate tubular member extending from a distal end of the body. The elongate tubular member may have an illumination path within a lumen of the elongate tubular member. The exemplary illumination device may further include an illumination source coupled to the illumination path and disposed within the inner chamber and a first illumination control disposed on the outer surface of the body. The first illumination control may permit the user to selectively control an adjustable illumination level between a high intensity state and a low intensity state.

An exemplary method of adjusting illumination used in an ophthalmic surgery may include receiving an input from a user to adjust an illumination level provided by an illumination device that may have an elongate tubular member extendable into a vitreous chamber of an eye. The elongate tubular member may include an optic fiber extending therethrough to provide illumination into the vitreous chamber. The input may be received via an illumination control disposed on an outer surface of the illumination device. The exemplary method may further include transmitting electrical signals to a surgical console, whereby the surgical console may cause an adjustment to illumination provided by an illumination subsystem of the console such that adjusted illumination passes through the optical fiber to the vitreous chamber of the eye.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and together with the description, serve to explain the principles of the present disclosure.

Figure 1:
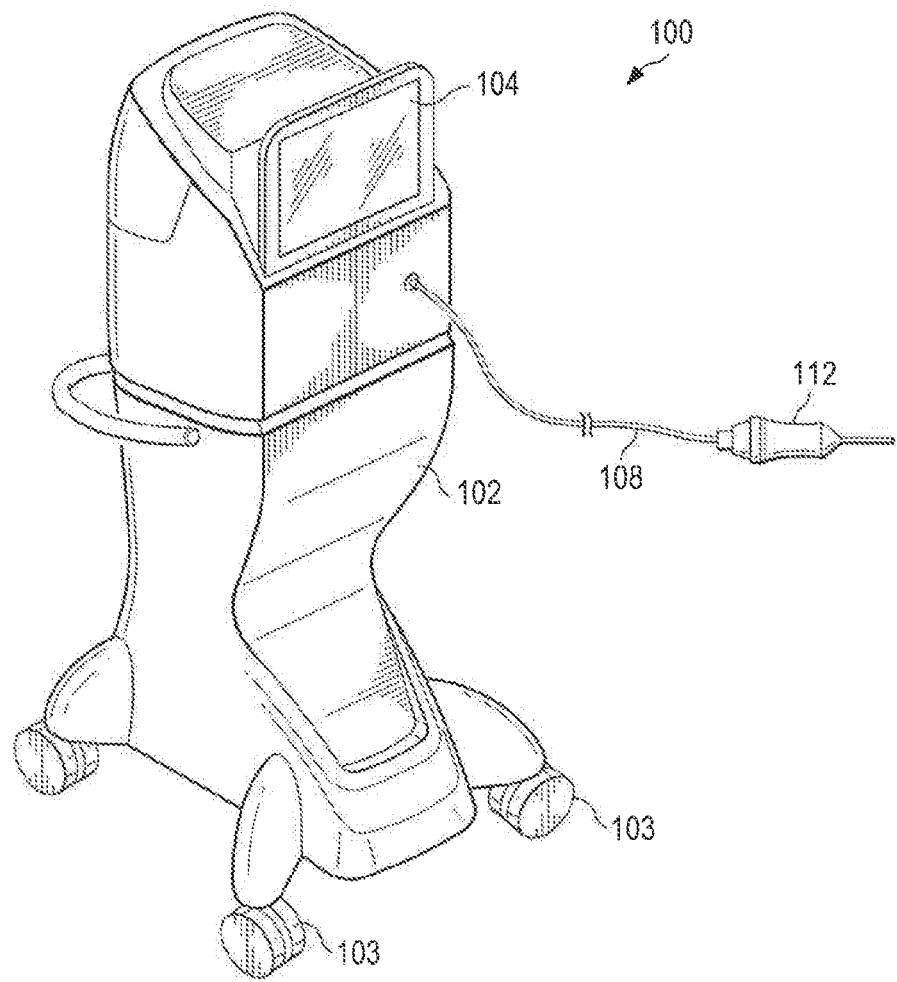
FIG. 1 illustrates a perspective view of an exemplary surgical system, according to aspects of the present disclosure.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended. For example, some more specific implementations of the present disclosure are directed to illumination devices usable in ophthalmic surgical treatments; however, the application of the principles of the present disclosure to illuminated devices usable in other surgical treatments is within the scope of this disclosure. Any alterations and further modifications to the described devices, instruments, methods, and any further application of the principles of the present disclosure are fully contemplated as would normally occur to one skilled in the art to which the disclosure relates. In particular, it is fully contemplated that some or all of the features, components, and/or steps described with respect to one implementation may be combined with some or all of the features, components, and/or steps described with respect to other implementations of the present disclosure. For simplicity, in some instances the same reference numbers are used throughout the drawings to refer to the same or like parts.

The present disclosure is directed to surgical systems and devices that provide illumination within a body cavity. During a surgical procedure, an illumination device may provide illumination by which other devices may be used to provide treatment to the body cavity. Conventionally, adjustments to the illumination provided by such an illumination device are made using a surgical console. Either the surgeon or an assistant interacts with interface elements on the surgical console to adjust aspects of the illumination including the level or intensity of illumination, the color of the illumination, and/or whether the illumination is in an on state or an off state.

For example, during a surgical procedure performed within an eye, the surgeon may first use illumination to visualize the transparent vitreous present within the vitreous chamber of the eye. The surgeon may need to visualize the vitreous in order to remove it to provide access to the retina. As the surgeon progresses toward the retina, the illumination may need to be dimmed to compensate for additional reflection off the retina. Using conventional tools, the surgeon may be required to look away from a microscope used to visualize the surgical site and turn his or her attention to the surgical console in order to adjust the illumination. Alternatively, the surgeon may orally communicate with an assistant to request that the assistant make adjustments to the illumination. In either case, the person making adjustments to the illumination is not visualizing the surgical environment as the adjustments are being made.

Implementations of the present disclosure include surgical illumination devices having a body with one or more hand- or finger-actuatable controls present on the device itself by which the user may manipulate the level of illumination, the color of illumination, and/or the state of an illumination source (i.e., an on state or an off state). In some implementations, the illumination controls may interact with a surgical console or with subsystems thereof to adjust the illumination. In other implementations, the illumination controls may interact with components of the illumination device itself. Combinations of such arrangements are also provided within the scope of this disclosure.

By allowing the surgeon to make adjustments without looking away from the surgical site, the ease and quality of the illumination adjustments may be improved. This may increase the efficiency and the efficacy of the various steps of a surgical operation being performed. Particularly, the illumination may be easily adapted by experimentation with illumination settings to access and discover illumination settings best suited for the present requirements. Because the surgical field is being viewed simultaneously with the adjustments, instant feedback may be provided on the quality of adjustments compared with previous settings.

FIG. 1 illustrates a surgical system 100, according to an exemplary implementation. The surgical system 100 includes a base housing or console 102 and an associated display screen 104 that may show data relating to system operation and performance during a surgical procedure. In some implementations, the console 102 may be mobile, for example including wheels 103 to facilitate movement as necessary. In an alternative implementation, the console 102 may not include wheels. The console 102 may include a plurality of subsystems that cooperate to enable a surgeon to perform a variety of surgical procedures, such as ophthalmic surgical procedures. For example, the console 102 may include an illumination subsystem with a light source producing light that can be directed into a body cavity to allow a surgeon to operate therein.

An exemplary surgical illumination device, which is illustrated as a handpiece 112, may attach to the console 102 and may form a part of the surgical system 100. In the illustrated implementation, the handpiece 112 is an illumination probe or illumination device used to provide illumination within the eye to facilitate an ophthalmic procedure. The handpiece 112 may be coupled to one or more subsystems included in the console 102, such as the illumination subsystem (described in more detail in connection with FIG. 2). In some implementations, the handpiece 112 is further coupled to a vitrectomy subsystem that controls a pump and/or a vacuum for use in the removal of vitreous. The vitrectomy subsystem may also provide power to and controls for handpiece 112. In some implementations, the handpiece 112 may be an oscillating vitreous cutter, with a fixed outer elongate tubular member with an oscillating inner elongate tubular member and with an integrated illumination feature. The system 100 may be used in various ophthalmic procedures, such as an anterior segment procedure, a posterior segment procedure, a vitreoretinal procedure, a vitrectomy procedure, a cataract procedure, and/or other procedures.

The handpiece 112 is coupled to the console 102 by a conduit 108. In some implementations, the conduit 108 provides a passageway for an optical fiber that passes from the illumination subsystem of the console 102 to the handpiece 112 to provide an illumination path. In such implementations, the conduit 108 may further include communication lines or wires that transmit control signals from the handpiece 112 to the console 102. Such control signals may include attenuation control signals and/or illumination color adjustment signals. Additionally, the control signals may include signals to cause the illumination subsystem to switch from an on state to an off state or from an off state to an on state.

Figure 2:
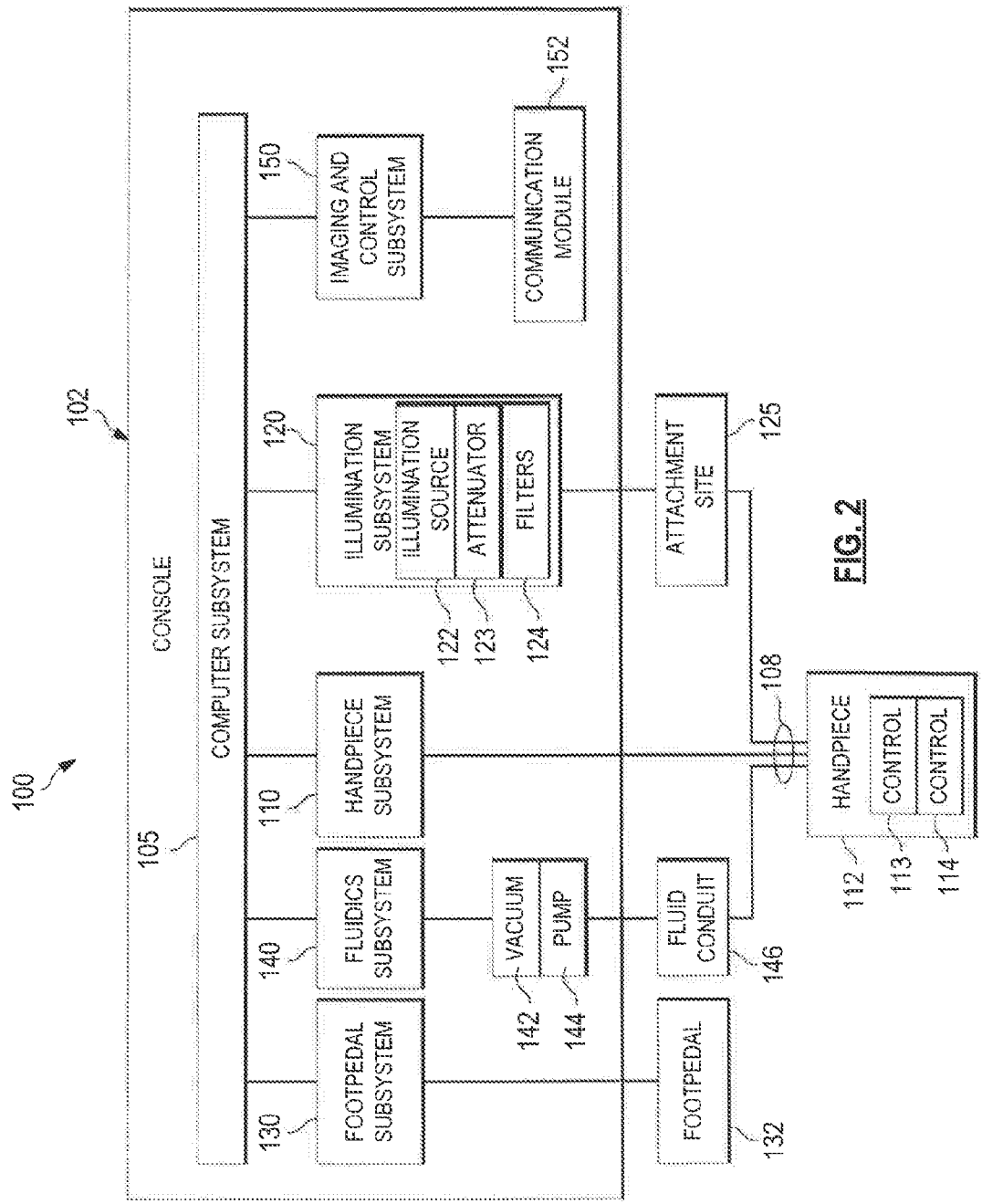
FIG. 2 is a block diagram of subsystems and components of the exemplary surgical system of FIG. 1, according to aspects of the present disclosure.

FIG. 2 is a block diagram of the surgical system 100 including the console 102 and several subsystems thereof. Some implementations of the surgical system 100 may omit one or more of the illustrated subsystems. The console 102 includes a computer subsystem 105, the display screen 104 (FIG. 1), and a number of subsystems that are used together to perform ocular surgical procedures, such as emulsification or vitrectomy surgical procedures, for example, and to provide illumination for these and other surgical procedures. The computer subsystem 105 may include one or more processing devices, such as a central processing unit or central processor or a microcontroller, and an information and data storage system. The data storage system may include one or more types of memory, such as RAM (Random Access Memory), ROM (Read Only Memory), flash memory, a disk-based hard drive, and/or a solid-state hard drive. The data storage system may store programmatic instructions for performing methods, functions, and operations described herein. The processing devices and storage system may communicate over a bus, which may also permit communication with and between one or more of the plurality of subsystems of the surgical system 100.

The surgical system 100 may include a handpiece subsystem 110 including the handpiece 112. The handpiece subsystem 110 may receive and/or encode/decode signals from and to the handpiece 112 for communication between the handpiece 112 and the computer subsystem 105 to enable the surgeon to use the handpiece 112 to control different subsystems included in the surgical system 100.

Implementations of the console 102 may include an illumination subsystem 120, which includes an attachment site 125 by which the conduit 108 couples the console 102 with the handpiece 112. The illumination subsystem 120 may include an illumination source 122. The illumination source 122 may include an incandescent light bulb, a halogen light bulb, a metal halide light bulb, a xenon light bulb, a mercury vapor light bulb, a light emitting diode (LED), a white laser, combinations thereof, and/or other light source. The illumination subsystem 120 may further include an attenuation system or attenuator 123 and one or more filters 124. The attenuator 123 may adjust an illumination level of the illumination provided by the illumination source 122. The filters 124 may alter or adjust a color composition of the illumination. For example, the filters 124 may include a bandpass filter that transmits light within a specified band of wavelengths. The filters 124 may include other filters that block a specified band of wavelengths.

The handpiece 112 may include one or more controls that may be used by the user to communicate with the illumination subsystem 120 and any or all of the components thereof. As illustrated, the handpiece 112 includes a first control 113 and a second control 114. The controls 113 and 114 may be positioned on an outer surface of the handpiece 112 to permit the user to adjust the level of illumination provided by the illumination subsystem 120, adjust a color composition of the illumination provided by the illumination subsystem 120, or cause the illumination source 122 to turn on or to turn off. More detailed implementations of the handpiece 112 and the controls 113 and 114 are provided herein.

Additional subsystems that may be included in implementations of the surgical system 100 may include a footpedal subsystem 130 including a footpedal 132, a fluidics subsystem 140 including an aspiration vacuum 142 and an irrigation pump 144 that connect to a fluid conduit 146. In implementations that include the fluidics subsystem 140, the fluid conduit 146 may provide a second connection to the handpiece 112 or may be run through a lumen within the conduit 108, such that a single conduit 108 couples the handpiece 112 to the console 102.

The surgical system 100 may further include an imaging and control subsystem 150 that has a communication module 152. The imaging and control subsystem 150 may facilitate communication between other subsystems, such as between the handpiece subsystem 110 and the illumination subsystem 120, for example. The communication module 152 may provide for wired and/or wireless communications including wireless communications such as Wi-Fi (wireless fidelity), Bluetooth, ZigBee, or radiofrequency identification (RFID) communications. Other tools may be included additionally or alternatively in other implementations.

To optimize performance of the different subsystems during surgery, their operating parameters may differ according to, for example, the particular procedure being performed, the different stages of the procedure, the surgeon's personal preferences and commands, whether the procedure is being performed in the anterior or posterior portion of the patient's eye, and so on.

The different subsystems in the console 102 comprise control circuits for the operation and control of the respective microsurgical instruments or instrument components, such as components of the handpiece 112. The computer subsystem 105 governs the interactions and relationships between the different subsystems to properly perform an ocular surgical procedure and to properly communicate information to the operator of the surgical system 100 through the display 104 and/or through a coupled microscope or wearable computing device.

In addition, the console 102 includes one or more input devices that permit a user to make selections within a limited scope to control or modify preprogrammed relationships between different subsystems. In this implementation, input devices may be incorporated into the console and may include the footpedal 132, a touch screen device responsive to selections made directly on the screen, a standard computer keyboard, a standard pointing device, such as a mouse or trackball, buttons, knobs, or other input devices are also contemplated. On the handpiece 112, the controls 113 and 114 may include one or more switches, knobs, touch-sensors, sliders, buttons, scroll-wheels, clickable scroll-wheels, etc., to enable a user to use the handpiece 112 as an input device to the console 102 as well. Using the input devices, a surgeon, scientist, or other user may select or adjust parameters that affect the relationships between the different subsystems of the console 102, such as the illumination subsystem 120. Accordingly, based on a user input, a user may change or adjust the relationships from those that were coded into the console by the system programmers. Further, a user may remap or reassign controls or other inputs according to the aspects of the procedure to be performed. For example, the user may manipulate the footpedal 132 to send a request to the imaging and control subsystem 150 to remap the controls 113 and 114 of the handpiece 112 to control the color of illumination by controlling the filters 124 and/or the illumination source 122 instead of controlling a level of illumination provided by the illumination subsystem by controlling the illumination source 122 and/or the attenuator 123. The footpedal 132 may be manipulated again by the user to revert back to the previous mapping of controls 113 and 114.

Other communications may be used to trigger remapping of the controls 113 and 114. For example, the control 113 may be used to alternate or select among functions that are controllable by the control 114. For example, the control 113 may be manipulated to indicate that signals from the control 114 should be interpreted to turn on or turn off the illumination source 122. The control 113 may be manipulated again so that the signals from the control 114 are interpreted to indicate modifications to a color composition of illumination from the illumination subsystem by interacting with the filters 124 and/or the illumination source 122 itself.

Figure 3:
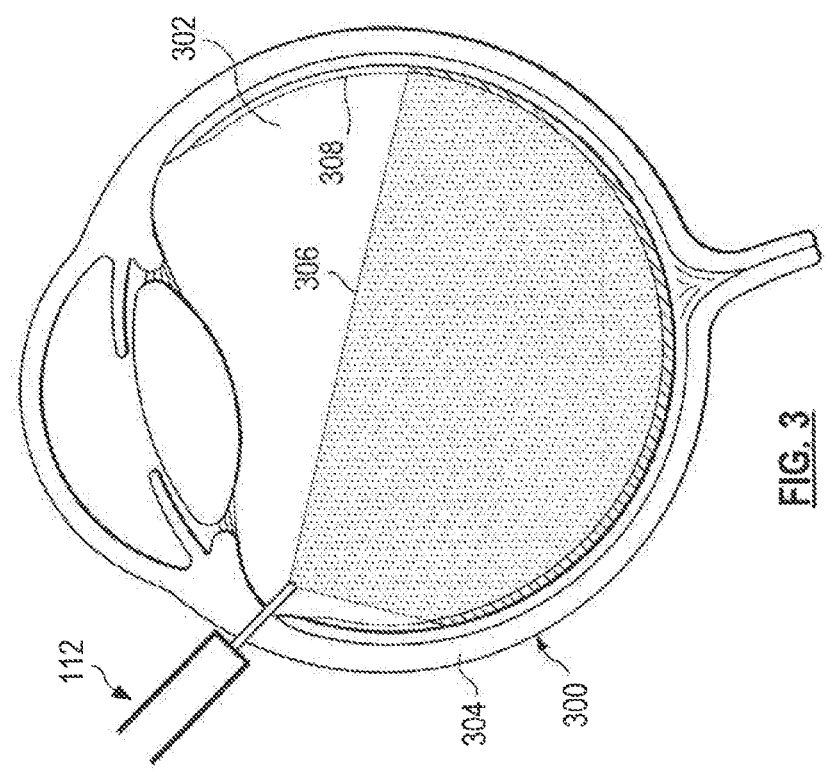
FIG. 3 shows an illumination device in situ in an eye, according to aspects of the present disclosure.

Referring now to FIG. 3, shown therein is a cross-sectional view of an eye 300. The eye 300 includes a vitreous chamber 302. A distal feature of the handpiece 112, which is described in further detail in connection with subsequent figures, is inserted through an incision formed in the sclera 304 of the eye 300. The distal feature of the handpiece 112 provides illumination 306 within the vitreous chamber. As illustrated in FIG. 3, the illumination 306 illuminates a portion of the vitreous chamber 302 and a portion of the retina 308 of the eye 300. The intensity and color of the illumination 306 may be changed as the user manipulates controls disposed on the outer surface of the handpiece 112 as described herein. In operation, additional surgical devices may be introduced into the vitreous chamber 302 through additional incisions made through the sclera 304. For example, in a vitrectomy procedure, a separate vitrectomy probe may be inserted through the sclera 304 to remove vitreous from the vitreous chamber 302. The illumination 306, provided by the handpiece 112, may permit a surgeon or other clinician to visualize the vitreous to facilitate removal thereof. As progress is made in removing vitreous, the location at which optimal illumination intensity or the color that is needed may change. The user may affect this change by using the controls 113 and/or 114 as shown in FIG. 2. As another example, a retinal manipulator may be inserted through the sclera 304. The illumination 306 may permit the surgeon to visualize the retina 308 to properly reposition a portion or portions thereof to treat a tear or a detachment. If reflection of the illumination off the retina becomes too intense, the user may use the controls 113 and/or 114 to change the color and/or intensity of the illumination to be able to better visualize the portion of the retina 308 to be manipulated or otherwise treated. For example, the change in color and/or intensity (e.g., from a high intensity to a lower intensity) may reduce glare produced by reflection off the retina or off one of the other surgical instruments being used in the procedure.

Figure 4:
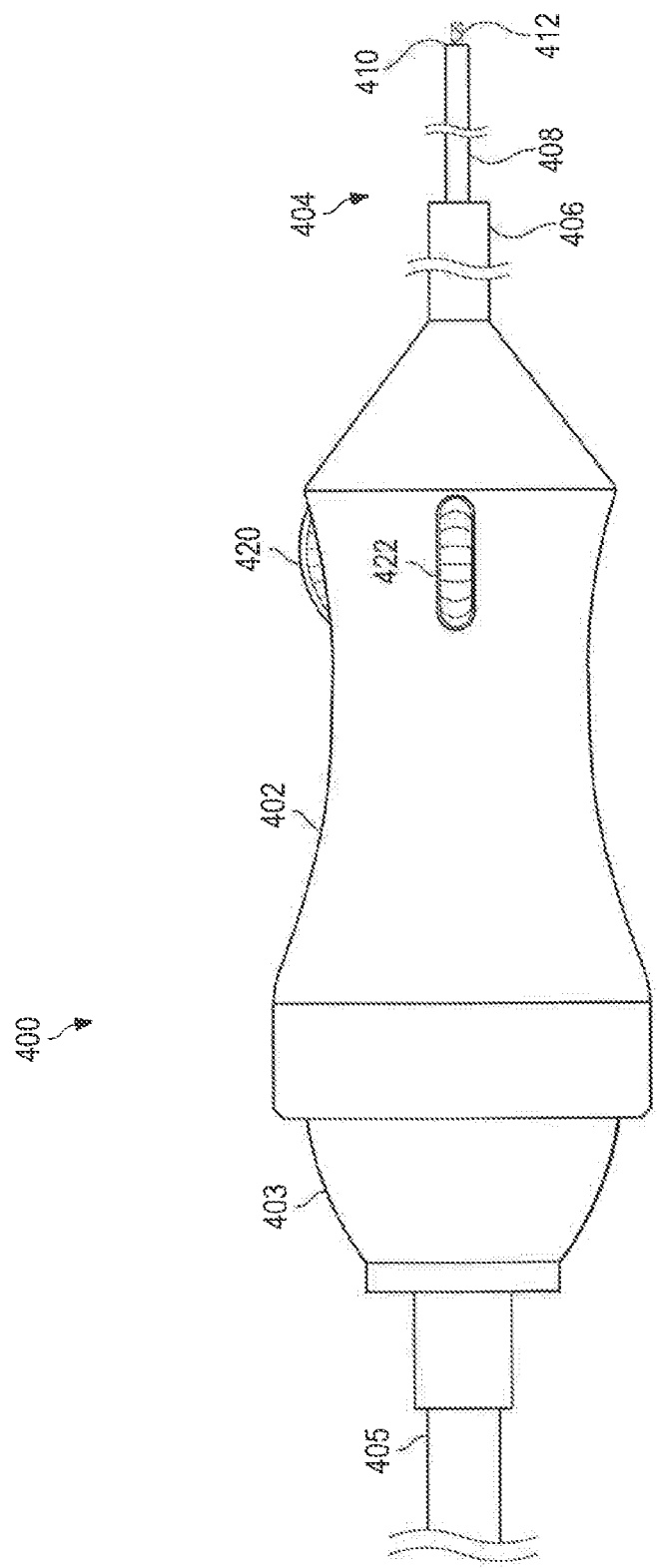
FIG. 4 is a side view of an illumination handpiece, which may be used as part of the exemplary surgical system of FIGS. 1 and 2, according to aspects of the present disclosure.

FIG. 4 illustrates a side view of an illumination device 400 that may correspond with the handpiece 112 as shown in FIGS. 1, 2, and 3. The illumination device 400 includes a housing or body 402 that is configured and sized to be held in the hand of a user, such as a surgeon, during the performance of a surgical procedure to provide illumination within a body cavity via a small entrance incision formed in a wall thereof. The body 402 may be formed from a rigid material, such as a rigid polymer or a metal. A user may manipulate the body 402, and thereby manipulate an elongate tubular section 404 extending therefrom. The body 402 may be a shell structure with an outer surface and an inner surface. The inner surface may define one or more chambers in which internal components of the illumination device 400 may be positioned and/or affixed.

The elongate tubular section 404 may include multiple portions through which illumination may travel to be provided into the body cavity. As illustrated, the elongate tubular section 404 includes an elongate collar 406 and a needle 408. The collar 406 may be a rigid elongate tubular member coupled to or formed as part of the body 402 to provide support to the needle 408. The needle 408 may be rigid as well, but may be more fragile that the collar 406. In some implementations, an outer diameter of the needle 408 may measure less than 4 mm (millimeters) or less than 3 mm. The needle 408 may be another elongate tubular member that extends from the body 402, a portion thereof extending within and through the collar 406.

As illustrated in FIG. 4, an illumination path 412 extends within the distal end 410 of the needle 408. The illumination path 412 may be provided by an optical fiber or by a lumen having a highly reflective surface therein. In some implementations, the illumination path 412 is a portion of an optical fiber that extends from the console 102 all the way to the distal end 410 of the needle 408. In other implementations, the illumination path 412 is a first optical fiber that extends within the elongate tubular section 404 and the body 402 and that couples to a second optical fiber that extends within the conduit 108 from the console 102 to the body 402. While the distal tip of the illumination path 412 is illustrated as extending or protruding beyond the distal end 410 of the needle 408, the distal tip of the illumination path 412 may be recessed within the needle 408 by an offset distance ranging from about 1 µm (micrometer) to about 20 µm in order to protect the distal tip of the illumination path from damage which may occur during insertion of the needle 408 into a body cavity, such as the eye 300 of FIG. 3. Additionally, while the illumination path 412 is illustrated as contained with the needle 408, other implementations of the illumination device 400 may include the illumination path 412 secured to the outside surface of the needle 408.

As illustrated in FIG. 4, the illumination device 400 includes a first control 420 and a second control 422. These may correspond to the controls 113 and 114 used to adjust illumination parameters and other features of the system 100. As illustrated, the first and second controls 420 and 422 may be scroll-wheel type controls that permit a user to provide an input from a range of inputs. For example, the first control 420 may be manipulated by the finger of a user to vary an intensity of illumination between a fully on state and a fully off state. In some implementations, the first control 420 may be scrolled or moved around an axis thereof in order to vary the intensity of the illumination. For example, the signals produced by the first control 420 may be communicated to the attenuator 123 of the illumination subsystem 120 of FIG. 2 to adjust the intensity of illumination as directed by the user to provide optimal illumination within the eye 300. The first control 420 may be "clicked" or pressed so that the rotational axis thereof moves orthogonally from a default position, generating a signal. This clicking input may be used to turn on or turn off the illumination source of the illumination device 400. In some implementations, the illumination source of the illumination device 400 may be the illumination source 122 as shown in FIG. 2.

The second control 422 may be manipulated by a finger of the user to adjust a color composition of the illumination produced by the illumination source. For example, the second control 422 may interact with the filters 124 of the illumination subsystem 120 (FIG. 2) to adjust a bandpass filter between higher and lower wavelengths of the light produced by the illumination source 122. In some implementations, the second control 422 may interact with the filters 124 to adjust a range of wavelengths transmittable through the bandpass filter. The second control 422 may also be a clickable scroll-wheel enabling the user to affect changes in the illumination by clicking the second control 422 in addition to scrolling therewith. For example, the user may click or press the second control 422 to engage or disengage the filters 124 of the illumination sub system 120.

The body 402 of the illumination device 400 may include an end portion 403 which serves to couple the illumination probe to a conduit 405. The conduit 405 may be the conduit 108 as illustrated in FIG. 1. Accordingly, the conduit 405 may mechanically couple the illumination device 400 to the console 102. Additionally, the conduit 405 may include electrical lines or wires that provide power to the illumination device 400 and to receive signals from the first and second controls 420 and 422, and additional controls included in some additional implementations of the illumination device 400.

In some implementations, the illumination device 400 may include other components that provide additional functionality to perform surgical procedures within the body cavity. For example, some implementations of the illumination device 400 may integrate a vitrectomy needle. For example, the needle 408 may include an integrated vitrectomy needle that may be activated to remove vitreous from the vitreous chamber 302 of the eye 300 of FIG. 3. In such implementations, the needle 408 may include an outer elongate tubular member and an inner elongate tubular member that oscillates within and relative to the outer elongate tubular member. In such implementations, the illumination path 412 may be disposed within or along the outer elongate tubular member to prevent the illumination path 412 from contacting the oscillating inner tubular member during a vitrectomy procedure. The illumination path 412 may provide illumination within the vitreous chamber 302 to permit a surgeon to visualize the vitreous as it is being removed by the vitrectomy needle.

In some other implementations, the needle 408 may include a port or opening (not explicitly shown) at the distal end 410 to permit an irrigation fluid to be introduced into the body cavity. For example, an irrigation fluid may flow through the needle 408 to ensure that the tip of the illumination path 412 remains clean during a surgical procedure or to clean an imaging device positioned near the distal end 410 of the needle 408. The irrigation fluid may also be used in an ophthalmic surgical procedure to maintain an appropriate pressure level within the eye 300. Accordingly, implementations of the illumination device 400 may integrate additional surgical tools and functionality. This may decrease a number of incisions to be made in the surface or wall of the body cavity, such as the sclera 304 of the eye 300, during a surgical procedure.

Figure 5:
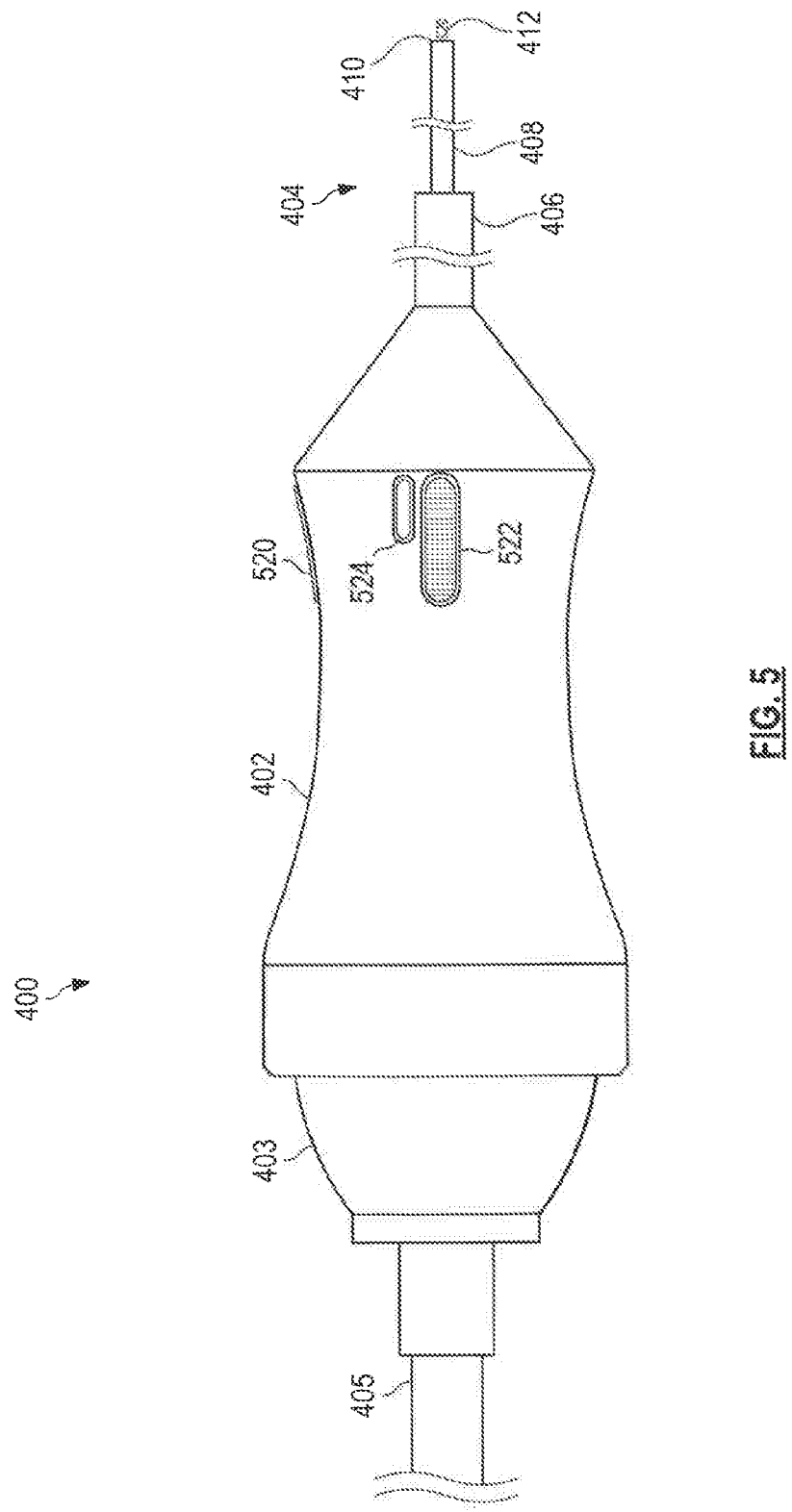
FIG. 5 is side view of another implementation of an illumination handpiece, which may be used as part of the exemplary surgical system of FIGS. 1 and 2, according to aspects of the present disclosure.

Referring now to FIG. 5, shown therein is another implementation of the illumination device 400. As shown in FIG. 5, the illumination probe includes the body 402 and the elongate tubular portion 404, with the collar 406, the needle 408, and the illumination path 412 extending therein or thereon. The illumination device 400 of FIG. 5 includes illumination controls 520 and 522. As illustrated, the illumination controls 520 and 522 may be touch-sensitive control panels. The illumination controls 520 and 522 may each include a plurality of capacitive sections configured in a linear arrangement. The illumination controls 520 and 522 may be used to vary between extremes of illumination and/or color, by tapping or swiping across the controls 520 and 522. Additionally, a two-position switch or button 524 (also referred to as illumination control 524) is disposed on the outer surface of the body 402. An inner surface of the body 402 defines an inner chamber, which may contain components that facilitate control of illumination and/or control of other surgical tools. The button 524 may be used to toggle between two illumination states, such as an on state and an off state. Signals produced by the controls 520 and 522 and by the button 524, which is also to be referred to herein as an illumination control, may be communicated wirelessly or via wired communication to the console 102. The signals may be received by the handpiece subsystem 110 and communicated over a bus of the computer subsystem 105 to the imaging and control subsystem 150. The communication module 152 may receive the signals. The signals may be interpreted or decoded by the imaging and control subsystem 150 and related via the computer subsystem 105 to the illumination subsystem 120. The illumination subsystem 120 may communicate the control signals to the illumination source 122, the attenuator 123, and/or the 124 as appropriate.

Figure 6:
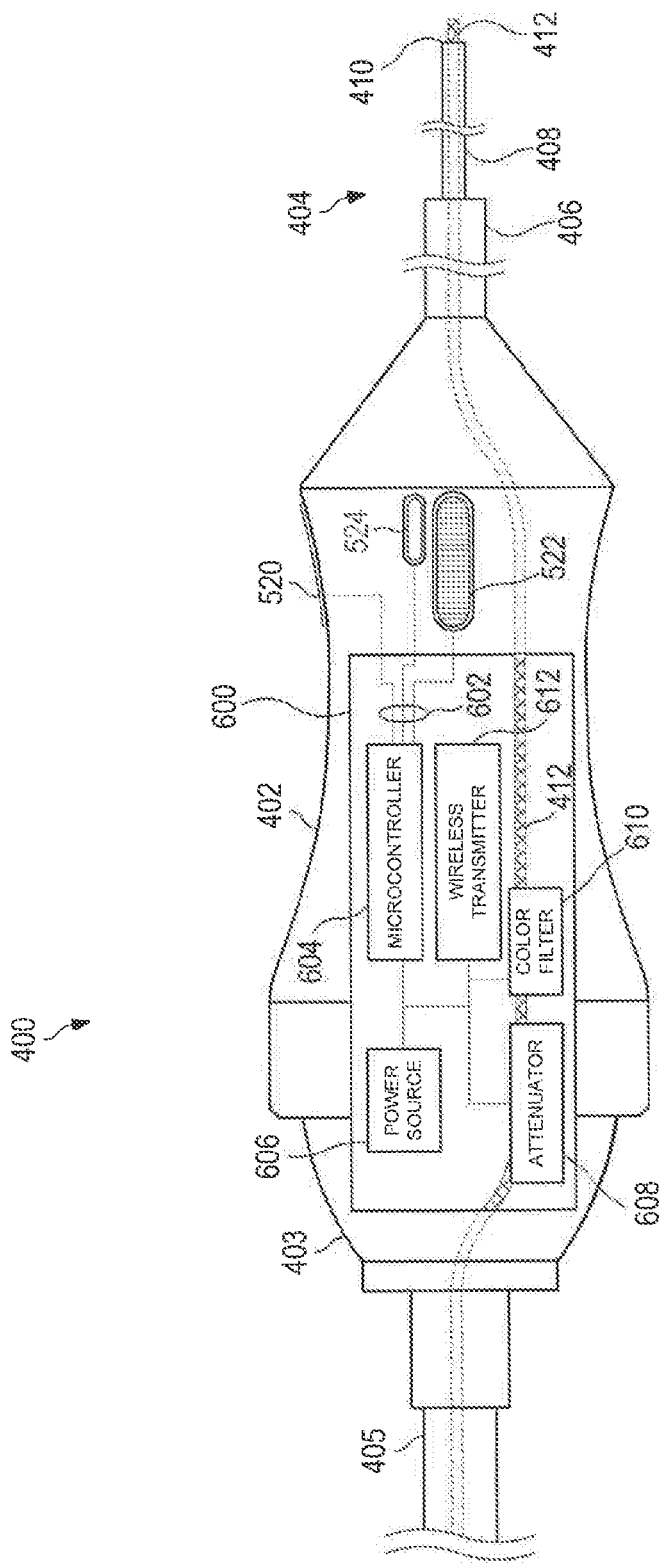
FIG. 6 is side view of the illumination handpiece of FIG. 5, further including a block diagram of components included therein, according to aspects of the present disclosure.

Referring now to FIG. 6, shown therein is the illumination device 400 according to the implementation illustrated in FIG. 5. Accordingly, a side view of the illumination device 400 is presented. Additionally, FIG. 6 includes a window 600 which illustrates a block diagram of components which may be contained within an inner chamber of the body 402 of the illumination device 400. As shown in FIG. 6, communication links 602 may couple the illumination controls 520 and 522 and the button 524 to a microcontroller 604. Some implementations of the illumination device 400 may not include the microcontroller 604. In such implementations, the communication links 602 may be wires that extend through the conduit 405 all the way to the console 102 of FIG. 1. The console 102 may receive the electrical signals generated by the illumination controls 520-524 directly in such implementations.

As illustrated, the microcontroller 604 may receive electrical signals produced by the illumination controls 520-524. The microcontroller 604 may generate control signals, which may be analog or digital control signals, based on the electrical signals received from the illumination controls 520-524. The illumination device 400 may include an internal power source 606, which may provide power to the illumination controls 520-524 so that the illumination controls 520-524 may produce electrical signals. The internal power source 606 may be a battery, a capacitor, or another suitable power source. Additionally, the power source 606 may provide power to the microcontroller 604.

As shown in FIG. 6, the illumination path 412 may be an optical fiber extending from the distal end 410 of the needle 408 through the body 402 (as seen in the window 600) and through the conduit 405 back to the console 102. The illumination path 412 may be coupled to the illumination source 122 at the attachment site 125 on the console 102. The implementation of the illumination device 400 shown in FIG. 6 includes an attenuator 608 and a color filter 610 disposed within the body 402. In such implementations, illumination provided by the illumination source 122 of the illumination subsystem 120 (FIG. 1) may be conveyed into the body 402 by the illumination path 412. Within the inner chamber of the body 402, the intensity of the illumination may be altered by the attenuator 608 and the color composition of the illumination may be altered by the color filter 610. Accordingly, signals received from the controls 520 and 522 may be received by the microcontroller 604 over the communication links 602 and relayed as control signals to the attenuator 608 to vary the illumination and to the color filter 610 to vary the color composition of the illumination. In some implementations, the attenuator 608 is provided by a neutral density filter or by another feature that limits or redirects a portion of the illumination emitted into the illumination path 412 by the illumination source 122.

As illustrated in FIG. 6, the window 600 includes a block representing a wireless transmitter 612. The wireless transmitter 612 may communicate with the communication module 152 as shown in FIG. 2. In implementations that do not include the attenuator 608 and the color filter 610, signals from the illumination controls 520-524 may be transmitted by the wireless transmitter 612 to the console 102. The corresponding control signals may be relayed to the appropriate components of the illumination subsystem 120 to effectuate the desired adjustments to the illumination. In implementations that include the attenuator 608 and the color filter 610, signals from the button 524 may be transmitted by the wireless transmitter 612 to the console 102 to change the illumination source 122 from an on state to an off state or from an off state to an on state.

Figure 7:
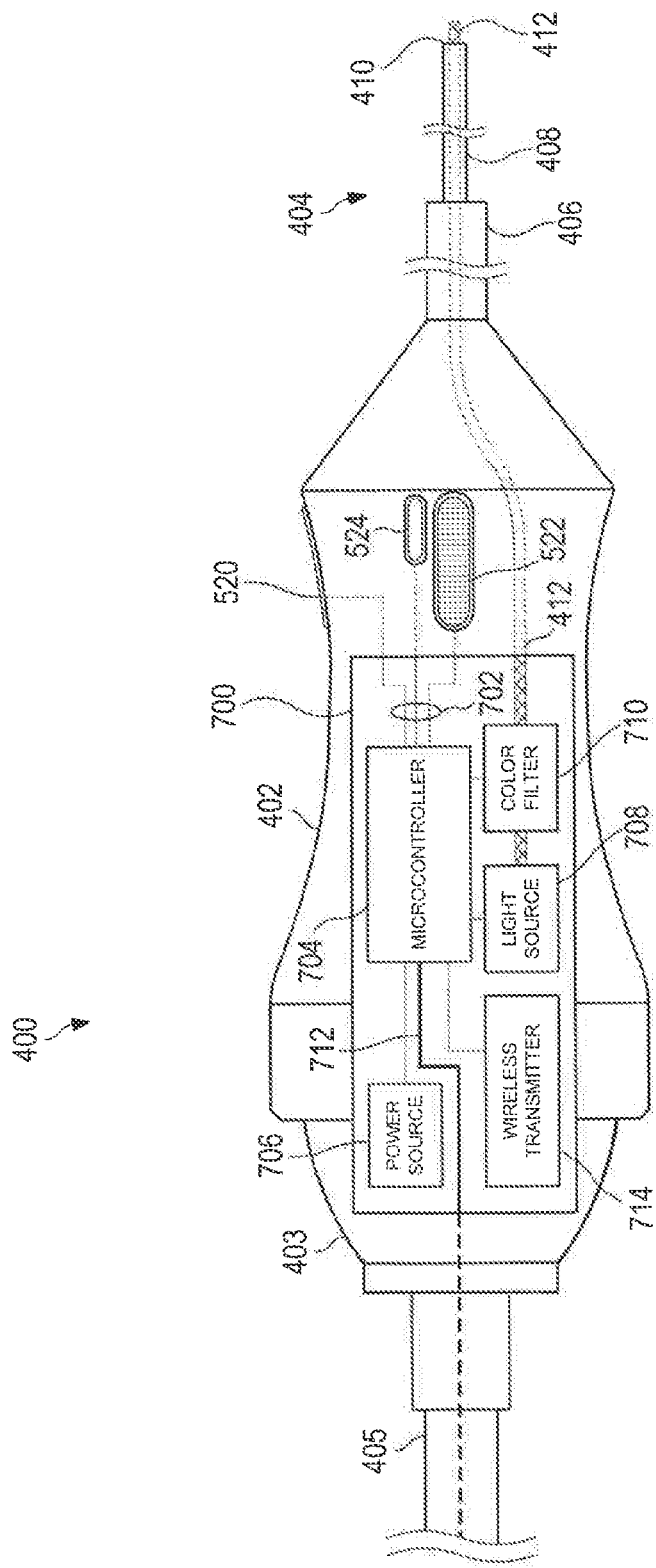
FIG. 7 is side view of the illumination handpiece of FIG. 5, further including another block diagram of components included therein, according to aspects of the present disclosure.

Referring now to FIG. 7, shown therein is another implementation of the illumination device 400. The implementation of FIG. 7 is a side view of the illumination device 400 including a window 700 illustrating a block diagram of components included within an inner chamber of the body 402. As shown in FIG. 7, the illumination controls 520-524 may communicate over the communication links 702 with a microcontroller 704. The microcontroller 704 may be powered by a power source 706. Unlike the implementation illustrated in FIG. 6, the implementation of illumination device 400 shown in FIG. 7 includes a light source 708 disposed within the inner chamber of the body 402. In such an implementation, the illumination source 122 of FIG. 2 may be omitted. The microcontroller 704 may receive electrical signals from the illumination controls 520-524 and generate corresponding control signals to interact with the light source 708 to turn the light source 708 on and off and to adjust an intensity thereof as well. Some implementations may include a separate attenuator. The light source 708 may be a light-emitting diode (LED), such as a white LED, an incandescent light bulb, or another suitable light source. In general, the amount of electrical power required by the light source 708 may be less than the amount of electrical power required by the illumination source 122 of the illumination subsystem 120 shown in FIG. 2, because the heat produced by the light source 708 may be more difficult to dissipate within or around the illumination device 400 than heat produced by the illumination source 122 within or around the console 102. Implementations of the illumination device 400 that include the light source 708 may include a fan and/or cooling fins coupled to the light source 708 to assist in dissipating the produced heat. The microcontroller 704 may further interpret electrical signals received from one or more of the illumination controls 520-524 to transmit control signals to the color filter 710, situated along the illumination path 412.

As illustrated in FIG. 7, the illumination device 400 may communicate with the console 102 via a wired communication link 712, which may couple the microcontroller 704 to the console 102 through the conduit 405 or via a wireless transmitter 714. In implementations that include the light source 708 and the color filter 710 within the inner chamber of the body 402, the communication link 712 and/or the wireless transmitter 714 may facilitate communication with the console for the operation of additional surgical tools and features included in the illumination device 400. For example, the illumination controls 520-524 may be used to control the light source 708 and color filter 710 while other controls disposed on the outer surface of the body 402 may be used to control a pulse rate of a vitrectomy needle or a flow of irrigation fluid. In some implementations, one or more of the illumination controls 520-524 may be used as controls for one or more such surgical tools.

The controls 520-524 may be remapped between one surgical function of the illumination device 400 and another. In some implementations, the two-position button 524 may be a sliding two-position button by which the surgeon may remap the illumination controls 520 and 522 to control other aspects of the illumination device 400. For example, in a first position of the two-position button 524, signals received by the microcontroller from the illumination controls 520 and/or 522 may be used to control the light source 708 and/or the color filter 710. In a second position of the two position button 524, the microcontroller 704 may generate control signals that are relayed or transmitted to the console 102 to interact with the vacuum 142 and/or the pump 144 of the fluidics subsystem 140. Accordingly, the illumination controls 520 and 522 may be remapped to permit the user to control additional functionality of an integrated illumination device 400. Some implementations may include a three-position button 524 which may be used to remap the controls to three different tools present in the illumination device 400.

Figure 8:
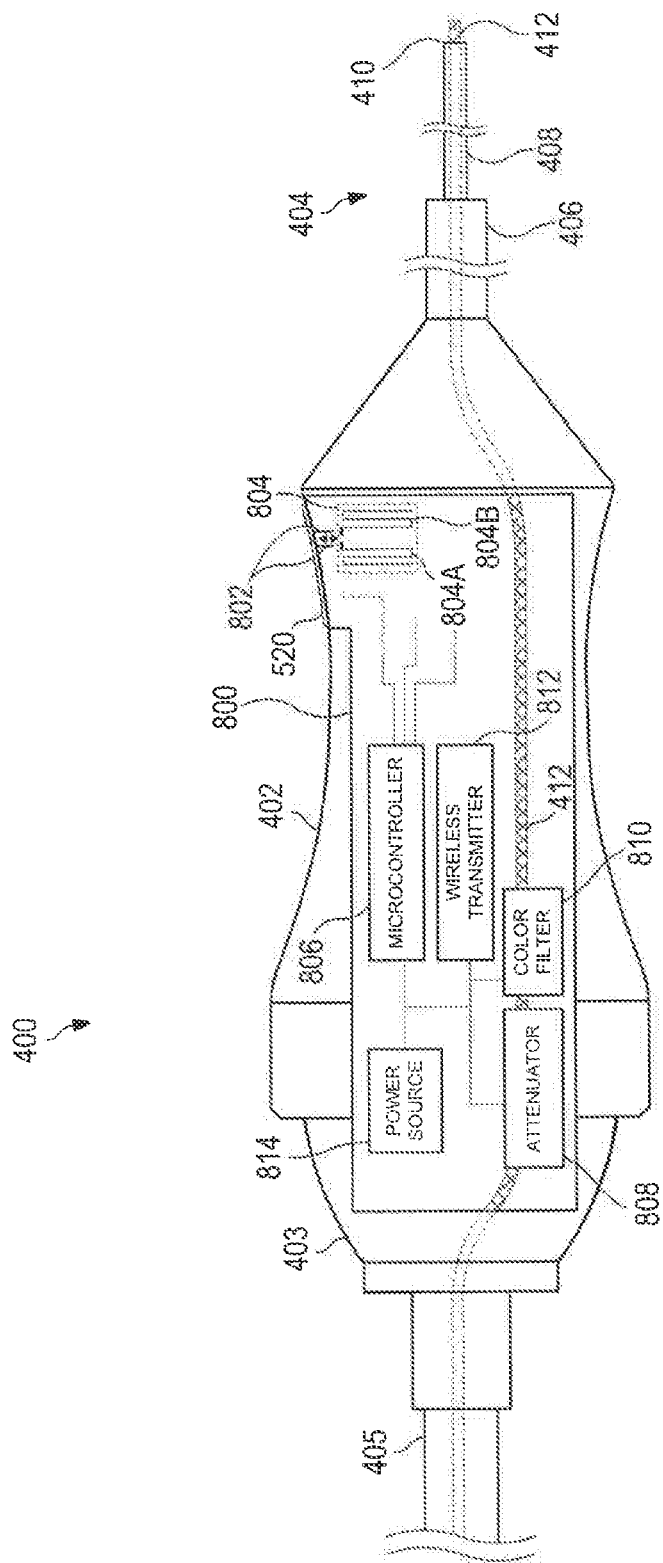
FIG. 8 is side view of the illumination handpiece of FIG. 5, further including another block diagram of components included therein, according to aspects of the present disclosure.

Referring now to FIG. 8, shown therein is yet another implementation of the illumination device 400. The implementation shown in FIG. 8 shares many of the features discussed with respect to implementations illustrated in FIGS. 4-7. A window 800 illustrates a block diagram of components included in the implementation of illumination device 400 of FIG. 8. The illumination control 520 may include electrical probes or conductors 802 that extend away from the generally planar surface of the illumination control 520. Actuation of the illumination control 520 by a finger of the user may cause the conductors 802 to couple a first radiofrequency identification (RFID) antenna component 804A to a second RFID antenna component 804B, collectively referred to as RFID component 804. An RFID reader may be disposed within the surgical environment in which the illumination device 400 is being used. The RFID reader may transmit power wirelessly to the RFID component 804. The RFID component 804 may respond with a signal that is read by the RFID reader. The signal depends on whether the first and second RFID antenna components 804A and 804B are coupled by the conductors 802 or not. Accordingly, a user may depress the illumination control 520, coupling the RFID antenna components 804A and 804B, and causing a change in a signal emitted by the overall RFID component 804. The change in the signal may be communicated to the surgical system 100. For example, the communication module 152 may be an RFID reader positioned to detect changes in a signal produced by the RFID component 804. When a change in the signal is detected, the imaging and control subsystem 150 may communicate to the illumination subsystem 120 to change the illumination source 122 from an on state to an off state or from an off state to an on state. Other signals received from illumination controls 522 and 524 may be interpreted by the microcontroller 806 to generate control signals to the attenuator 808 and/or the color filter 810. As another example, the change in the signal produced by the RFID component 804 may be interpreted by the imaging and control subsystem 150 to generate an attenuator control signal causing the attenuator 123 to increment or decrement an intensity setting of the illumination subsystem 120. Some implementations of the illumination device 400 as illustrated in FIG. 8 may further include a wireless transmitter 812 and a power source 814, as described herein with respect to other implementations of the illumination device 400.

Combinations of the features and functions described herein with respect to the various implementations illustrated and described with respect to FIGS. 4, 5, 6, 7, and 8 may be apparent to one of ordinary skill in the art after careful study of the present disclosure. Such combinations are within the scope of the present disclosure. For example, implementations of the illumination device 400 may include a clickable scroll-wheel, like the control 420, and a capacitive touch control, like the control 522.

Figure 9:
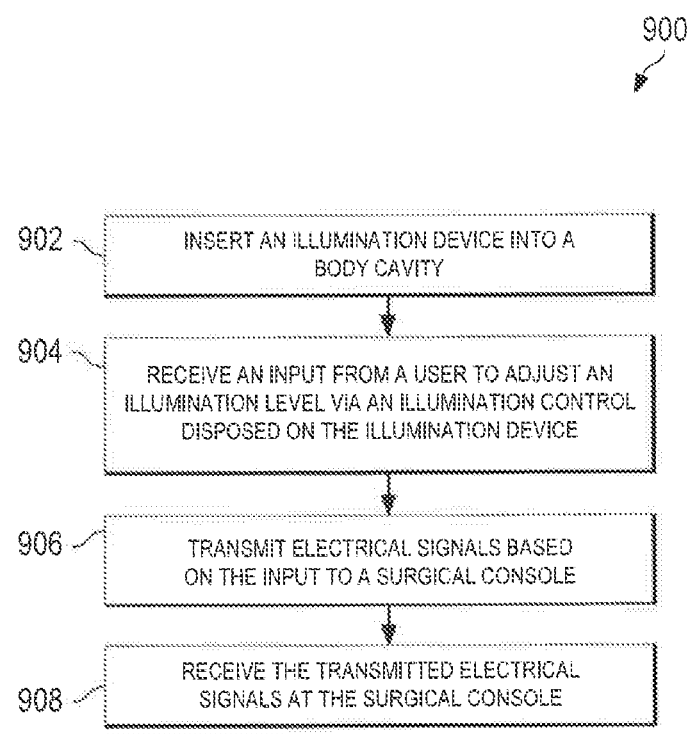
FIG. 9 is a method of utilizing the exemplary surgical system of FIG. 1, according to aspects of the present disclosure.

Referring now to FIG. 9, shown therein is a method 900 of utilizing an illumination device such as an implementation of the illumination device 400 and/or the handpiece 112 as described herein and as illustrated in FIGS. 1-8. As illustrated in FIG. 9, the method 900 includes a plurality of steps or operations. Implementations of the method 900 may include additional steps or operations before, after, in between, or as part of the enumerated operations shown in FIG. 9. Additionally, some implementations of the method 900 may omit one or more of the enumerated operations.

At 902 (FIG. 9), an illumination device is inserted into a body cavity. For example, a portion of the handpiece 112 may be inserted through an incision formed in the sclera 304 to position the portion of the handpiece 112 within the vitreous chamber 302 of the eye 300 (FIG. 3). In implementations of the handpiece 112, such as the illumination device 400 of FIGS. 4-8, the needle 408 may be inserted through the sclera 304 so that the illumination path 412 may provide illumination 306 within the vitreous chamber 302.

At 904 (FIG. 9), an input may be received from a user to adjust an illumination level provided by the illumination device. For example, the illumination device 400 may include a rigid needle 408 that protects the illumination path 412 and facilitates careful positioning thereof. The illumination path 412 may be an optical fiber and may couple to either the illumination source 122 of FIG. 2 or a light source 708 contained within a body 402 of the illumination device 400 to provide illumination 306 within the eye 300 (FIG. 3). The input may be received via an illumination control, such as one or more of the illumination controls 520-524 (FIG. 5) or the illumination controls 420 and 422 (FIG. 4).

At 906 (FIG. 9), electrical signals are transmitted based on the input of 904. The electrical signals may be transmitted to a surgical console, such as the surgical console 102 of FIGS. 1 and 2. The electrical signals may be transmitted over wires or communication links directly from the illumination control or, in other implementations, the electrical signals may be received by a microcontroller and interpreted thereby to produce a control signal which may be the electrical signal transmitted to the console 102. The control signals may be transmitted wirelessly via a wireless transmitter such as the wireless transmitter 714 of FIG. 7 or the control signals may be transmitted from the microcontroller via a wired communication link, such as the communication link 712, which extends through the conduit 405 to the console 102.

At 908 (FIG. 9), the electrical signals received by the surgical console 102 may cause the surgical console to adjust illumination provided by the illumination subsystem 120 of the console 102 such that an adjusted illumination passes through the illumination path 412 into the vitreous chamber 302 of the eye 300 of FIG. 3.

In some implementations, one of the transmitted electrical signals may include a request to remap other transmitted electrical signals to control a second illumination aspect instead of a first illumination aspect. For example, the control 524 (FIG. 5) may be pressed by a user of the illumination device 400 and a corresponding signal may be sent to the console 102. The console 102 may interpret the signal as a request to remap the control 522 from controlling the attenuator 123 to controlling the filters 124. In other implementations, the request to remap the transmitted electrical signals may be a request to remap the electrical signals to control an aspect of the illumination device 400 other than illumination aspect. For example, the control 524 may be pressed by the user to cause the controls 520 and 522 to control and irrigation fluid system, such as fluidics subsystem 140 rather than the illumination subsystem 120.

Additionally, some implementations of the method 900 may include detecting a change in an RFID signal. The change in the RFID signal may be produced when an illumination control includes conductors, such as the conductors 802 of FIG. 8 that couple and decouple portions of an RFID component 804, modifying an RFID antenna. The change in the RFID signal may be detected by an RFID reader, such as the communication module 152. The change in the RFID signal may be interpreted as a request to adjust an aspect of the illumination subsystem 120 as described herein.

Implementations of the present disclosure may include hand-held illumination devices with integrated illumination controls. Methods of utilizing such devices are also described herein. By interacting with an illumination source through the controls present on an outer surface of the hand-held illumination devices, a surgeon may be able to more carefully control illumination to optimize visualization for a particular stage of a surgical procedure. The surgeon may directly control aspects of illumination, such as intensity and/or color composition, rather than communicating with an assistant to ask the assistant to affect such changes and rather than looking away from the surgical site to interact with a console to implement the changes. Accordingly, implementations of the present disclosure may make surgical procedures more efficient and more effective.

In that regard, although illustrative implementations have been shown and described, a wide range of modifications, changes, and substitutions is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An illumination system for use in performing an ophthalmic surgical procedure, the illumination system comprising:
   a body configured to be held by a hand of a user, the body comprising an outer surface and an inner surface, the inner surface defining an inner chamber;

an elongate tubular member extending from a distal end of the body, the elongate tubular member having an illumination path within a lumen of the elongate tubular member;

an illumination source coupled to the illumination path through an optical fiber extending between the body and a surgical console; and a plurality of illumination controls disposed on the outer surface of the body, comprising:
- a first illumination control permitting the user to selectively control an adjustable illumination level between a high intensity state and a low intensity state; and
- a second illumination control permitting the user to selectively control a color composition of light produced by the illumination source;

wherein at least one of the first or second illumination control is also configured to control at least one of aspiration or irrigation when a user input is received to switch the first or second illumination control to control the at least one of aspiration or irrigation.

2. The illumination system of claim 1, further comprising a microcontroller to receive signals from the illumination controls disposed on the outer surface of the body, and wherein the microcontroller generates and transmits control signals to the surgical console.

3. The illumination system of claim 2, wherein the console comprises an illumination subsystem that includes an illumination attenuator and an illumination color adjustment mechanism.

4. The illumination system of claim 2, further comprising:
an illumination attenuator disposed within the inner chamber and coupled to the microcontroller, the microcontroller generating attenuator control signals based on the signals received from the first illumination control disposed on the outer surface of the body, wherein the illumination attenuator adjusts the illumination level according to the attenuator control signals.

5. The illumination system of claim 4, further comprising a color filter disposed within the inner chamber and coupled to the microcontroller, the microcontroller generating illumination color adjustment signals in response to signals received from the illumination controls that cause the color filter to adjust the color composition of the light produced by the illumination source.

6. The illumination system of claim 1, wherein the illumination path comprises an additional optical fiber that connects to the optical fiber to receive illumination from the illumination source.

7. The illumination system of claim 1, further comprising a wireless transmitter disposed within the inner chamber, wherein the wireless transmitter is coupled to the illumination controls and transmits signals received from the illumination controls to the surgical console.

8. The illumination system of claim 7, wherein the wireless transmitter is a passive radiofrequency identification (RFID) component and actuation of the one of the illumination controls causes a change in an antenna of the RFID component.

9. The illumination system of claim 1, wherein the illumination controls are coupled to an illumination subsystem of the surgical console by wires extending between the illumination controls and the illumination subsystem, such that signals generated by the illumination controls are transmitted to a microcontroller included in the illumination subsystem.

10. The illumination system of claim 1, wherein the plurality of illumination controls comprise a plurality of capacitive sections on the body to receive user input.

11. An illumination device configured to provide illumination in a body cavity during a surgical procedure, the illumination device comprising:
a body configured to be held by a hand of a user, the body comprising an outer surface and an inner surface, the inner surface defining an inner chamber;

an elongate tubular member extending from a distal end of the body, the elongate tubular member having an illumination path within a lumen of the elongate tubular member;

an illumination source coupled to the illumination path and disposed within the inner chamber; and a first illumination control disposed on the outer surface of the body, the first illumination control permitting the user to selectively control an adjustable illumination level between a high intensity state and a low intensity state; and a second illumination control permitting the user to selectively control a color composition of light produced by the illumination source;

wherein at least one of the first or second illumination control is also configured to control at least one of aspiration or irrigation when a user input is received to switch the first or second illumination control to control the at least one of aspiration or irrigation.

12. The illumination device of claim 11, further comprising a microcontroller disposed within the inner chamber to receive signals from a plurality of illumination controls disposed on the outer surface of the body, the illumination controls including the first illumination control.

13. The illumination device of claim 12, further comprising an illumination attenuator disposed within the inner chamber and coupled to the microcontroller, the microcontroller generating attenuator control signals based on the signals received from the first illumination control of the plurality of illumination controls disposed on the outer surface of the body, wherein the illumination attenuator adjusts the illumination level according to the attenuator control signals.

14. The illumination device of claim 12, further comprising a color filter disposed within the inner chamber and coupled to the microcontroller, the microcontroller generating illumination color adjustment signals in response to signals received from one of the plurality of illumination controls that cause the color filter to adjust the color composition of light in the illumination path.

15. The illumination device of claim 11, wherein the elongate tubular member comprises an outer member and an inner member, the inner member connected to an oscillator to cause the inner member to oscillate relative to the outer member to cut material received into a port formed in a distal end of the outer member.

16. The illumination device of claim 11, further comprising a power source disposed within the inner chamber, the power source supplying power to the illumination source and to the first illumination control.

17. The illumination device of claim 11, further comprising a microcontroller disposed within the inner chamber, the microcontroller receiving first signals from the first illumination control and receiving programming signals from a surgical console, wherein the programming signals cause the microcontroller to interpret the first signals as controlling an illumination color instead of the illumination level.

18. An illumination device configured to provide illumination in a body cavity during a surgical procedure, the illumination device comprising:
- a body configured to be held by a hand of a user, the body comprising an outer surface and an inner surface, the inner surface defining an inner chamber;
- an elongate tubular member extending from a distal end of the body, the elongate tubular member having an illumination path within a lumen of the elongate tubular member;
- an illumination source coupled to the illumination path and disposed within the inner chamber; and
- a first illumination control disposed on the outer surface of the body, the first illumination control permitting the user to selectively control an adjustable illumination level between a high intensity state and a low intensity state;
- wherein the first illumination control comprises a rotational control having an axis that is displaceable orthogonally to the axis, wherein the rotation control generates a first signal type and displacement generates a second signal type.

19. The illumination device of claim 18, further comprising a microcontroller disposed within the inner chamber to receive signals from a plurality of illumination controls disposed on the outer surface of the body, the plurality of illumination controls including the first illumination control.

20. The illumination device of claim 19, further comprising an illumination attenuator disposed within the inner chamber and coupled to the microcontroller, the microcontroller generating attenuator control signals based on the signals received from the first illumination control of the plurality of illumination controls disposed on the outer surface of the body, wherein the illumination attenuator adjusts the illumination level according to the attenuator control signals.

21. The illumination device of claim 19, further comprising a color filter disposed within the inner chamber and coupled to the microcontroller, the microcontroller generating illumination color adjustment signals in response to signals received from one of the plurality of illumination controls that cause the color filter to adjust a color composition of light in the illumination path.

* * * * *